United States Patent [19]

Bauer

[11] Patent Number: 5,141,511
[45] Date of Patent: Aug. 25, 1992

[54] RESORPTIVE BONE CERAMIC ON THE BASIS OF TRICALCIUM PHOSPHATE

[75] Inventor: Gerd Bauer, Darmstadt, Fed. Rep. of Germany

[73] Assignee: Merck Patent Gesellschaft mit Beschraenkter Haftung, Darmstadt, Fed. Rep. of Germany

[21] Appl. No.: 476,207

[22] Filed: Feb. 7, 1990

[30] Foreign Application Priority Data

Feb. 8, 1989 [DE] Fed. Rep. of Germany ....... 3903695

[51] Int. Cl.$^5$ ................................................ A61F 1/08
[52] U.S. Cl. ......................................... 623/16; 623/66
[58] Field of Search ..................... 623/16, 66; 424/423

[56] References Cited

U.S. PATENT DOCUMENTS

| | | | |
|---|---|---|---|
| 3,787,900 | 1/1974 | McGee | 3/1 |
| 3,929,971 | 12/1975 | Roy | 623/16 |
| 4,113,500 | 9/1978 | Ebihara et al. | 106/39.5 |
| 4,373,217 | 2/1983 | Draenert | 3/1.9 |
| 4,626,392 | 12/1986 | Kondo et al. | 623/16 |

OTHER PUBLICATIONS

Unilab Surgibone for Surgical Implant, Unilab, Inc.
Treatment of Jaw Defects with Demineralized Bone Implants, Kaban et al., Osteotech, pp. 623–626, Jun. 6, 1989.
Bioceramic Implants in Surgically Produced Infrabony Defects, Nery et al., Bioceramic Implants, Journal of Periodontol, Jun. 1975.

Primary Examiner—David Isabella
Assistant Examiner—Gina Gualtieri
Attorney, Agent, or Firm—Millen, White & Zelano

[57] ABSTRACT

The invention relates to a process for the preparation of a resorptive bone ceramic on the basis of tricalcium phosphate which can be used as a bone replacement material. In the process, natural bone material, freed from the soft tissues, is used as the starting material. The remaining organic substances are removed from this starting material by pyrolysis. The remaining bone material, which consists virtually completely of hydroxyapatite, is subsequently treated with a phosphate carrier and then subjected to a sintering step.

15 Claims, No Drawings

RESORPTIVE BONE CERAMIC ON THE BASIS OF TRICALCIUM PHOSPHATE

SUMMARY OF THE INVENTION

The invention relates to a process for the preparation of resorptive bone ceramic on the basis of tricalcium phosphate, which can be used as a bone replacement material.

A high-performance material for medical implants nowadays is expected to meet the requirement of, on the one hand, a high mechanical stability and, on the other hand, a high biological activity, that is to say, of being accepted by the organism and integrated in it. In the case of bone replacement material, this means that it is intended to fuse within a short time with body tissue, in particular with the bone.

Compositions for implants on a mineral basis usually only guarantee a high mechanical stability when they are employed as ceramics, i.e., in the form of materials, or components, which have been sintered at sufficiently high temperatures.

It is known that bone replacement material which is made of natural bone material is more readily accepted and penetrated by body tissue. Bone ceramic is highly bioactive, in particular when their porous fine structure, which is characteristic of natural bone, remains intact. For this purpose, it is necessary to remove all organic substances from the natural bone material, if possible in such a manner that the mineral matrix remains unchanged. The latter must then be sintered to give bone ceramic.

In known processes, soft tissues are first removed mechanically, and a considerable proportion of organic material is then removed from the bone material by chemical treatment, for example using hydrogen peroxide solution. Apart from the fact that such treatments are complicated and require precautionary measures, for example because of the bleaching action of hydrogen peroxide, the procedure does not succeed in removing the organic material from the bone structure. Admittedly, the remaining organic material can be burned by subsequent pyrolysis of the bone at increased temperatures; but volatile constituents can occur in such amounts that this results in damage to the fine structure of the bone matrix. In this context, it must be taken into account that the mechanical strength of the bone matrix is only achieved during the sintering process; before the sintering process, in contrast, the matrix has only a very low mechanical stability.

To prepare bone ceramic while maintaining the porous structure of natural bone completely intact, it is therefore necessary that complete removal of organic substances be possible under particularly mild conditions.

Natural bone material, in its mineral phase, consists virtually completely of hydroxyapatite (abbreviated to HA hereafter), a calcium phosphate of the empirical formula $Ca_5(PO_4)_3OH$. The procedures outlined above, or analogous procedures, up to the calcined bone ceramic, do not cause any chemical changes in the mineral phase, that is to say, the latter is also present as HA in the end product.

Implants and bone replacement material on the basis of HA are regarded as essentially non-resorptive in the organism. This means that the alien material remains virtually unchanged over a long period. Bone ceramic of this type, however, has a lower mechanical strength than naturally-grown, endogenous bone.

For this purpose, it would be considerably more favorable to have available materials which, after being integrated in the bone tissue and fused with the endogenous bone, are relatively rapidly resorbed and replaced by newly-formed, endogenous bone substance.

It is known that materials on the basis of tricalcium phosphate (abbreviated to TCP hereafter) of the empirical formula $Ca_3(PO_4)_2$ are highly resorptive in the organism under certain circumstances. To this end, the material must have gone through a high-temperature treatment, such as, for example, in the manufacture of sintered ceramic. In the cooling-down phase, a phase change in the crystal modification occurs in TCP at a temperature of 1125° C., which is accompanied by a sudden decrease in volume of more than 7%. This necessarily leads to considerable tensions and microruptures in the structure of the material. In consequence, the ceramic is soon degraded in the organism to fine particles, the material then being resorbed by body-specific lysis mechanisms and hence being metabolized and, finally made available for the synthesis of new, endogenous bone substance.

Known materials of this type on the basis of TCP, however, are not made from natural bone wherein the porous tine structure of natural bone remains intact.

The invention is therefore based on the particular demand for a bone ceramic which combines the material characteristics of a ceramic which is made from natural bone while maintaining tho porous structure intact, but which usually substantially comprises HA, with the resorption qualities of TCP.

It has now been found that such a resorptive bone ceramic on the basis of tricalcium phosphate, which can be used as a bone replacement material, can be prepared in such a manner that natural bone material which has been freed from soft tissues is used as the starting material, the remaining organic substances are removed from this starting material by pyrolysis, the remaining bone material which usually substantially comprises hydroxyapatite is subsequently treated with phosphate carrier and then subjected to a sintering step.

The process according to the invention is characterized in that the soft tissues are first removed, the bone material is then dried at an increased temperature of not more than 150° C., the temperature is then increased to about 550° C. in a reducing atmosphere or an atmosphere deficient in air, the bone material is in a next step brought to a temperature of between 550° and 800° C. under an excess of air, cooled, then treated with such a stoichiometric amount of phosphate carrier as is required for converting it into tricalcium phosphate, followed by a sintering step at temperatures of between 1125° and 1670° C.

The invention relates to a process characterized as above, for the preparation of a resorptive bone ceramic on the basis of tricalcium phosphate.

The invention also relates to a resorptive bone ceramic which is a sintered ceramic material, made from natural bone material, comprising: tricalcium phosphate, wherein the porous fine structure, as is characteristic of natural bone, remains completely intact.

The process according to the invention is composed of two main steps, namely pyrolysis of the organic proportion of natural bone material which proceeds under particularly mild conditions and during which the porous fine structure of the bone remains completely intact, and of a specific conversion of the mineral phase of the pyrolyzed bone material which comprises HA, into TCP by treatment with phosphate carrier, followed by sintering.

The first main step of the process according to the invention is carried out in such a way that the soft tissues are first removed and the bone material is then dried at an increased temperature of not more than 150° C., the temperature is subsequently increased to about 550° C. in a reducing atmosphere or an atmosphere deficient in air, and, in the next step, the bone material is brought to a temperature of between 550° and 800° C. in an excess of air.

To carry out the drying step under as mild conditions as possible, it is advantageous to dry the bone for between 12 and 72 hours at an increased temperature of not more than 150° C. Furthermore, it is advantageous to increase the drying temperature gradually from ambient temperature to the maximum temperature 150° C. Gradually in this context means that the increase takes place continuously over the entire drying period. This avoids sudden evaporation at the boiling point of water, which might damage the bone material. A gradual increase in temperature results in constant evaporation of the highly volatile components over the entire drying period, no substantial evolution of gas taking place in this process.

By the fact that the bone material after the drying process is subjected to an increased temperature of up to about 550° C. in a reducing atmosphere or an atmosphere deficient in air, pyrolysis takes place, i.e., thermal decomposition of the organic material, which results in carbonization of the organic bone material with volatile components being eliminated. In this context, it is advantageous to treat the bone for about 8-24 hours under a reducing atmosphere or an atmosphere deficient in air. During this process the temperature is preferably gradually increased to 550° C., gradually in this connection also meaning that the temperature is increased constantly over the entire treatment period. This measure also contributes to the formation of gas components of different volatilities in succession, so that no undesirable vigorous evolution of gas occurs at any point in time. In the next step, the carbon is combusted at temperatures of not more than 800° C. in an excess of air. Highly volatile components are no longer present in this pure combustion process, so that damage to the inorganic bone matrix is avoided.

Burning the bone material in an excess of air at a temperature of 550°-800° C. preferably 750° to 800° C. is preferably carried out over 1 to 24 hours, it being advantageous again to gradually increase the temperature to about 800° C. while the bone is burned.

The described process of a mild pyrolysis has the advantage that no chemical treatment whatsoever of the bone material is necessary, but that, after the soft tissues have been removed mechanically, the bone material is subjected exclusively to a heat treatment which is divided into different sections. The mineral bone matrix thus obtained has the unaltered fine structure of the bone material employed and still usually substantially comprises HA.

In the second main step of the process according to the invention, the chemical composition of the mineral phase of the pyrolyzed bone material is converted from HA to TCP. For this purpose, the material is treated with a stoichiometrically appropriate amount of a phosphate carrier and subsequently subjected to a sintering step.

A conversion which is similar in principle, of HA of natural origin to TCP and/or other calcium phosphates, is disclosed in U.S. Pat. No. 4,861,733. This patent describes the preparation of porous bone replacement material in which the mineral matrix is of marine origin (corals). The process described in this patent is disadvantageous inasmuch as it comprises two chemical conversion steps of the material, namely, first a hydrothermal conversion of the natural calcium carbonate material into HA and, subsequently, the conversion into TCP and/or other calcium phosphates by treatment with phosphate carriers and sintering. A specific stoichiometric conversion to virtually exclusively TCP ceramic is not possible using the described process, or at least not provided. A further serious disadvantage is that, due to the marine origin of its starting material, this material cannot have the fine structure typical for natural bone, nor the trace element distribution of natural bone.

According to the invention, the conversion of the pyrolyzed bone material comprising HA in its mineral phase into TCP is carried out by treatment with a phosphate carrier and sintering. Suitable phosphate carriers are in principle all phosphate-containing compounds which can be thermally decomposed in such a way that they transfer virtually only their $P_2O_5$ content to the HA material. Preferably, such compounds are phosphoric acid, ammonium dihydrogen phosphate, diammonium hydrogen phosphate or triammonium phosphate. At increased temperatures, these compounds eliminate water, or water and ammonia; the $P_2O_5$ proportion remains essentially in the mineral phase, the stoichiometry of the latter being shifted from HA to TCP. A phosphorusrich calcium phosphate of the stoichiometric composition $CaO \times 2P_2O_5$ has proved a particularly favorable and therefore preferred phosphate carrier, whose application virtually excludes $P_2O_5$ losses due to sublimation, which means that the end product comprises a mineral phase converted virtually completely into TCP.

The cooled, pyrolyzed bone material is treated with the phosphate carrier, preferably in the form of an aqueous solution, for which process the required amounts and concentrations in the specific case can be determined by simple stoichiometric calculations. The treatment is carried out by imbibing and drying the material. This is followed by the high-temperature treatment at temperatures of between 1125° and 1670° C., during which process the phosphate carrier is decomposed, HA is converted into TCP and the ceramic is sintered. Sintering is preferably carried out over a period of 2-6 hours at temperatures of between 1150° and 1400° C. In this process too it is advantageous to gradually increase the temperature to the sintering temperature. This is followed by cooling, preferably slowly over a period of 2-6 hours.

The resulting bone ceramic has the material characteristics, in particular mechanical strength, as is typical of high-fired, sintered ceramic materials. Since, according to the invention, it is prepared with the natural porous fine structure of the bone starting material remaining virtually completely intact, it has a high bioactivity which is demonstrated by rapid and intensive penetration and fusion with endogenous tissue. Since it comprises TCP, it is moreover resorptive, so that it is soon replaced by newly-formed, Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Federal Republic of Germany P 39 03 695.2, filed Feb. 8, 1989, are hereby incorporated by reference.

Natural bone material generally has a hydroxyapatite content of at least about 80%, usually at least about 90% by weight, with respect to the mineralphase of the bone. The resultant bone ceramic produced by the process according to the invention has a TCP content of at least about 80%, preferably at least about 90%, e.g., more than about 95 wt.%, as determined by X-ray analysis.

EXAMPLES

Example 1

Beef bone was partly freed from its organic constituents by boiling. Any adhering soft tissues were removed mechanically. The material was given the desired shape by comminution by means of a saw.

Drying was then carried out over a period of 26 hours with a continuous increase in temperature from room temperature to 150° C. Pyrolysis of the organic constituents was effected by raising the temperature to 550° C. at a rate of 20° C./h, under an atmosphere deficient in air. The material was then brought to 800° C. in an excess of air at a rate of 25° C./h.

After cooling, the material was imbibed with 33% by weight of aqueous solution of 40.8% of $(NH_4)_2HPO_4$ and dried. Sintering was effected over 4 hours at 1250° C. after the temperature had been raised at a rate of 100° C./h.

The resulting bone ceramic has a TCP content of more than 95% as determined by x-ray analysis.

Example 2

Beef bone was prepared and pyrolyzed as in Example 1.

After cooling, it was imbibed with 33% by weight of an aqueous solution containing 200 g of $CaO \times 2\ P_2O_5$ (prepared from $Ca(H_2PO_4)_2 \times H_2O$ and $H_3PO_4$ in the molar ratio 1:2) per liter, and dried.

Sintering was effected over 4 hours at 1250° C. after the temperature had been raised at a rate of 100° C./h.

The resulting bone ceramic has a TCP content of more than 95% as determined by x-ray analysis.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of a tricalcium phosphate resorptive bone ceramic, wherein natural bone material is separated from soft tissues, and remaining organic substances are removed by pyrolysis, and resulting bone material is subsequently treated with phosphate carrier and then subjected to a sintering step, said process comprising:
   removing tissues from natural bone material;
   drying the bone material for a predetermined period at an increased temperature of not more than about 150° C.;
   thereafter increasing the temperature to about 550° C. in a reducing atmosphere or an atmosphere deficient in air;
   heating the bone material to a temperature of about 550° C.-800° C. under an excess of air, which is in excess of that needed for removal of remaining organic substances by pyrolysis;
   cooling the bone material;
   treating the bone material with a stoichiometric amount of phosphate carrier to convert hydroxyapatite into tricalcium phosphate; and
   sintering the resultant material at a temperature of about 1125°-1670° C.

2. A process according to claim 1, wherein said predetermined period of drying is about 12-72 hours at an increased temperature of not more than about 150° C.

3. A process according to claim 2, wherein, during the drying step, the temperature is gradually increased from ambient temperature to the maximum temperature of about 150° C.

4. A process according to claim 1, wherein, after the drying step, the temperature is gradually increased to about 550° C. in a reducing atmosphere or an atmosphere deficient in air.

5. A process according to claim 1, wherein, after the bone material is heated to about 550° C., the bone material is kept for about 1-24 hours at a temperature of about 550° C.-800° C. in an excess of air.

6. A process according to claim 5, wherein, after the bone material is heated to about 550° C., the temperature is gradually increased up to about 800° C. in an excess of air.

7. A process according to claim 1, wherein, after pyrolysis and cooling have been effected, the material is treated with an aqueous solution of a phosphate carrier and then dried.

8. A process according to claim 7, wherein said phosphate carrier is from the group consisting of phosphoric acid, ammonium dihydrogen phosphate, diammonium hydrogen phosphate and triammonium phosphate.

9. A process according to claim 7, wherein said phosphate carrier is a phosphorus-rich calcium phosphate of the stoichiometric composition $CaO \times 2\ P_2O_5$.

10. A process according to claim 1, wherein sintering is effected over a period of about 2-6 hours and at a temperature of about 1150°-1400° C.

11. A process according to claim 10, wherein the temperature is gradually increased to the sintering temperature.

12. A process according to claim 5, wherein, after the bone material is heated to about 550° C., the bone material is kept for about 1-24 hours at a temperature of about 750°-800° C. in an excess of air.

13. A tricalcium phosphate resorptive bone ceramic produced by the process according to claim 1.

14. A process for preparation of tricalcium phosphate resorptive bone ceramic, comprising:

sintering tricalcium phosphate bone material at a temperature of about 1125°-1670° C. wherein said material is derived from natural bone material which has been dried at an increased temperature, for a predetermined period, of not more than about 150° C., thereafter treated at a further increased temperature of not more than about 550° C. in a reducing atmosphere or air-deficient atmosphere, heated under an excess of air, which is in excess of that needed for removal of remaining organic substances by pyrolysis, at a temperature of about 550° C.-800° C., cooled and then treated with a stoichiometric amount of phosphate carrier to convert the hydroxyapatite of the bone material to tricalcium phosphate.

15. A resorptive bone ceramic comprising tricalcium phosphate:

said ceramic material consisting essentially of sintered tricalcium phosphate which results from treated hydroxyapatite derived from natural bone material and wherein the porous fine structure, characteristic of natural bone, remains intact.

* * * * *